United States Patent [19]

Kawashima et al.

[11] 4,025,391

[45] * May 24, 1977

[54] PREPARATION OF BEAD-SHAPED IMMOBILIZED ENZYME

[75] Inventors: Koji Kawashima, Chofu; Keiji Umeda, Tokyo, both of Japan

[73] Assignee: Director of National Food Research Institute, Tokyo, Japan

[ * ] Notice: The portion of the term of this patent subsequent to June 8, 1993, has been disclaimed.

[22] Filed: Dec. 4, 1975

[21] Appl. No.: 637,672

Related U.S. Application Data

[63] Continuation-in-part of Ser. No. 585,488, June 10, 1975, abandoned.

[30] Foreign Application Priority Data

June 15, 1974 Japan .............................. 49-67640

[52] U.S. Cl. .............................. 195/68; 195/31 F; 195/63; 195/DIG. 11; 204/159.22
[51] Int. Cl.² .................................... C07G 7/02
[58] Field of Search ................ 195/63, 68, DIG. 4, 195/31 F; 204/159.15, 159.16, 159.22

[56] References Cited

UNITED STATES PATENTS

| 3,081,244 | 3/1963 | Campanile | 204/159.15 |
|---|---|---|---|
| 3,137,643 | 6/1964 | Bell et al. | 204/159.22 |
| 3,859,169 | 1/1975 | O'Driscoll et al. | 195/63 |
| 3,933,587 | 1/1976 | Maeda et al. | 195/63 |

FOREIGN PATENTS OR APPLICATIONS 1,955,638  6/1970  Germany

OTHER PUBLICATIONS

Nilsson, et al., The Use of Bead Polymerization of Acrylic Monomers for Immobilization of Enzymes, Biochimica et Biophysica Acta., vol. 268, 1972 (pp. 253–256).

*Primary Examiner*—David M. Naff
*Attorney, Agent, or Firm*—Flynn & Frishauf

[57] ABSTRACT

Bead-shaped immobilized enzymes are obtained by adding a solution containing an enzyme and at least one water-soluble monomer or polymer to a water insoluble or slightly soluble fluid to form a mixture having enzyme-containing beads therein, freezing the mixture at −200° C to −5° C and subjecting the resultant frozen mixture to ionizing radiation under aerobic conditions to polymerize the monomer or polymer and produce polymer beads containing enzymes immobilized therein. The polymer beads are strong enough to be packed in a column, and continuous enzyme reactions can be carried out with enzymes immobilized in the polymer beads.

6 Claims, No Drawings

PREPARATION OF BEAD-SHAPED IMMOBILIZED ENZYME

CROSS REFERENCE TO OTHER APPLICATION

This application is a continuation-in-part of our co-pending application Ser. No. 585,488, filed on June 10, 1975, now abandoned.

BACKGROUND OF THE INVENTION a. Field of the Invention

The present invention relates to a process for producing a bead-shaped immobilized enzyme by adding a solution containing an enzyme and a water-soluble monomer or polymer to a water-insoluble or slightly soluble fluid to form a bead-shaped solution and subjecting the solution to ionizing radiation to polymerize the monomer or polymer.

b. Description of the Prior Art

Heretofore, several methods for producing an immobilized enzyme have been described. However, an enzyme product obtained by conventional methods cannot be utilized in an enzyme-column process. It is necessary to establish a method of immobilizing an enzyme efficiently and also to provide a process of forming a bead-shaped immobilized enzyme. Combining both processes skillfully for making a continuous enzyme reaction using an enzyme-column has been difficult.

SUMMARY OF THE INVENTION

It is an object of the present invention to provide a process for producing a bead-shaped immobilized enzyme.

It is another object of the present invention to provide a continuous process involving enzyme reaction by the use of an enzyme preparation of this invention packed in a column.

DETAILED DESCRIPTION

The present invention relates to a process for producing a bead-shaped immobilized enzyme by adding a solution containing an enzyme and a water-soluble monomer or polymer to a water-insoluble or slightly soluble fluid to form a bead-shaped solution and imparting ionizing radiation to the solution in order to polymerize the monomer or polymer.

The enzymes applicable in this invention are not only purified or crude enzymes, but also microorganisms per se. Specifically, suitable enzymes are amylase, protease, lipase, acylase, D-amino acid oxidase, catalase, various kinds of dehydrogenase, urease, ribonuclease, glucose isomerase, glucose oxidase and the like.

In the present invention, the enzyme can be combined in advance with a water-soluble or insoluble carrier such as water-soluble dextran, CM cellulose, a anhydrous maleic acid polymer, a polypeptide, a styrene derivative polymer, agalose, cellulose, dextran, starch and the like, in order to improve stability of the enzyme.

Water-soluble monomers contemplated herein include acrylamide, acrylic acid, methacrylic acid, sodium acrylate, potassium acrylate, calcium acrylate, magnesium acrylate, ferrous acrylate, cobalt acrylate, nickel acrylate, magnesium methacrylate, ferrous methacrylate, cobalt methacrylate, nickel methacrylate, acrylonitrile, propylene glycol, pyrrolidone, 1-vinyl-2-pyrrolidone and diacetone acrylamide. Further, water-soluble monomers such as diethyl amino ethyl methacrylate and divinyl sulfone can be used with the above monomers. Similarly, water-soluble polymers such as polyvinyl alcohol having a polymerization degree of 1400, polyvinyl pyrrolidone and the like, can be used.

As to a water-soluble polymer such as polyvinyl alcohol having a polymerization degree of 1400, it is a polymer having a molecular weight small enough to be soluble in water and one which can be polymerized with ionizing radiation, to a large molecular weight and water-insoluble polymer. The resulting water-insoluble polymer may be a homopolymer or a copolymer or a mixture thereof.

These monomers or polymers can be used singly or by combining two or more of them. Further, the concentration of monomer or polymer solutions is not critical, and thus the concentration can be selected freely. Also, N,N'-methylene bis-acrylamide and divinyl sulfone can be added as a cross-linking agent in suitable quantities.

Water-insoluble or slightly water-soluble fluids, oils and solvents can be used. Typical oils are vegetable oils such as soybean oil, seasame oil, olive oil; mineral oils such as volatile oils, kerosene and light oils. Typical solvents include aliphatic hydrocarbons such as n-hexane, petroleum ether; aromatic hydrocarbons such as toluene, xylenes; alcohols higher than propyl alcohols such as butyl alcohol, amyl alcohols; ethers such as ethyl ether; esters such as ethyl acetate; ketones such as methyl ethyl ketone. Further, a surface active agent can be added, if desired.

In the present invention, a fluid of which solubility in water is at most about 15% can be used as a slightly water-soluble fluid. As the an example of such a fluid, iso-butanol and ethyl ether are shown.

Further, gasolines having boiling points of about 30°–200° C can be used as volatile oils.

A monomer or polymer solution containing an enzyme is added to said fluid while agitating the fluid or adding the solution dropwise by means of a nozzle; as a result, a bead-shaped solution is formed. The size of the beads is influenced by the diameter of the nozzle, pressure of injection, speed of agitation and viscosity of the fluid. When a surface active agent is added to the fluid, beads with smaller size can be obtained easily. Generally, the size of the beads is from 0.1 to 30 mm, preferably 1 to 10 mm.

When the monomer or polymer solution containing an enzyme is added to a fluid, the resulting bead-shaped solution is preferably frozen by a proper coolant. The coolant used in this invention should cool the fluid below −5° C., generally from −5° to −200° C., and preferably −20° to −80° C. For this purpose, dry ice-acetone, liquid nitrogen, dry ice-ethyl alcohol and $CaCl_2 \cdot 6H_2O$-ice mixtures and the like are used.

Finally, radio polymerization is conducted by ionizing irradiation. A bead-shaped immobilized enzyme is obtained. As ionizing radiation sources $Co^{60}$, $Cs^{137}$ X-rays and accelerated electrons are applicable. The irradiation dose is 30–1000 Krad, preferably between 40 and 600 Krad. Radiation polymerization of monomers such as acrylamide previously has been conducted anaerobically, because oxygen inhibits the polymerization process, but in this invention irradiation can be conducted aerobically. After the irradiation process including cooling, the resulting bead-shaped polymer is thawed (melted), washed and obtained as a bead-shaped immobilized enzyme.

The immobilized enzyme prepared by this invention is bead-shaped and is mechanically strong enough to be packed in a column. Thus, it is possible to prepare immobilized enzyme columns.

Before conducting irradiation when the fluid is frozen, a spongy bead-shaped preparation is obtainable. This product is stable and has high enzymatic activity. Publications so far reported on this subject report bead-shaped immobilized enzyme preparations by using bead-shaped carriers such as glass beads or polystyrene beads. Enzymes are bound covalently to these beads. However, in the present invention, such a carrier is not required. The bead-shaped immobilized enzyme obtained has a spongy texture when the bead-shaped solution in the fluid is frozen before the irradiation step and thus has a large surface area.

In the present invention, the bead size of the immobilized enzyme is not necessarily small for the purpose of increasing the surface area. Even a relatively large bead-shaped immobilized enzyme exhibits fairly high activities.

EMBODIMENTS OF THE INVENTION

EXAMPLE 1

Reagents A, B, C and D were prepared.
A. Acrylamide (30 g) and N,N'-methylene bis-acrylamide (1.6 g) in 100 ml distilled water;
B. 30% aqueous solution of sodium acrylate;
C. 30% aqueous solution of calcium acrylate;
D. 2 mg/ml solution of invertase enzyme.

One ml of reagents A, B and D were mixed with 2 ml of reagent C and hereafter are referred to as enzyme monomer solution. 300 ml of soybean oil was taken in a large test tube (5 cm diameter) and immersed in a coolant of dry ice-acetone so that the oil in the lower part of the tube was frozen while the oil on the top of the tube was not frozen. The enzyme monomer solution was injected into the oil dropwise, and thus was frozen in the oil in bead form. All of the oil was then frozen. In this state, the frozen enzyme monomer solution was radio copolymerized by $Co^{60}$ gamma rays, with a dose of 83.2 Krads. Then at room temperature the mixture was melted, filtered, washed with detergent and water, resulting in bead-shaped immobilized invertase with diameters ranging from 1 to 10 mm.

For the purpose of measuring the activity of the immobilized enzyme, 1/50th of it was used. To this, 1 ml of 10% sucrose solution and 9 ml of citrate phosphate buffer (pH 3.8) were added, and reacted at 40° C. for 20 minutes. The resulting glucose content was measured by the Willstatter-Schudel method.

For comparison purposes, 1 ml of native invertase (10 $\mu$g/ml) was reacted similarly, at pH 4.5, and resulting glucose was assayed.

As a result, bead-shaped immobilized invertase of 1-2 mm in diameter showed a retained activity of 55.1%, while those with a diameter of 3-7 mm had a retained activity of 35.2%.

Enzyme activity is expressed as residual activity. It can be calculated according to the following formula:

$$\frac{\text{Enzyme activity after immobilization}}{\text{Enzyme activity before immobilization}} \times 100 \, (\%)$$

EXAMPLE 2

25 mg of glucoamylase, 2 ml of 30% aqueous acrylamide, 2 ml of 30% aqueous sodium acrylate and 0.1 ml of divinyl sulfone were mixed and, as in Example 1, injected to cooled oil and radio copolymerized with a dose of 550 Krad. This resulting mixture was melted at room temperature (about 20° C.) and bead-shaped immobilized glucoamylase was obtained.

For measuring the activity, 1/50th of above immobilized glucoamylase beads of 2-5 mm diameter was washed with detergent and water. To this was added 2 ml citrate buffer (pH 5.0), 6 ml of distilled water, and 1 ml 2% soluble starch solution. The resulting mixture was reacted at 40° C. for 20 minutes.

Resulting reducing sugar was assayed by the Willstatter-Schudel method. For comparison, native glucoamylase (100 $\mu$g/ml) was reacted similarly, and the resulting reducing sugar was assayed. The bead-shaped immobilized glucoamylase showed 7.4 % of retained activity.

EXAMPLE 3

Two ml of reagent A in Example 1, 2 ml of 20% aqueous 1-vinyl-2-pyrrolidone, 1 ml of glucose oxidase (0.5 mg/ml) were mixed and injected into cooled olive oil and prepared as in Example 1.

A bead-shaped immobilized enzyme of 1-6 mm diameter was thus obtained. Activity thereof was determined with 1/25th of bead-shaped immobilized enzyme to which were added 5 ml of tris buffer (pH 7.0) containing o-dianisidine, 1 ml of peroxidase and 2 ml of 5% glucose. The resulting mixture was reacted at 37° C. for 60 minutes. Reaction was stopped by adding 8 ml of 5N-HCl. Optical density was measured at 525 m$\mu$.

For comparison 1 ml of native glucose oxidase (10 $\mu$g/ml) was reacted similarly. As a result, bead-shaped immobilized glucose oxidase showed 18.4% retained activity.

EXAMPLE 4

The same procedure was followed as in Example 3. The one difference was substitution of 10% hydroxy ethyl methacrylate for 1-vinyl-2-pyrrolidone and D-amino acid oxidase (50 mg/ml) for glucose oxidase. The irradiation dose was 500 Krad instead of 83.2 Krad.

The bead-shaped immobilized D-amino acid oxidase (1-6 mm in diameter) was washed with a detergent and water, 1/10th of this was weighed and 5 ml borate buffer (pH 8.3, 1/20M), 1 ml of catalase (3mg/25 ml) and 1 ml of 100 mm dl-alanine were added. Reaction was conducted at 30° C. for 60 minutes. Resulting pyruvic acid was measured.

For comparison, native D-amino acid oxidase (2.5 mg/ml) was similarly reacted. As a result, bead-shaped immobilized D-amino acid oxidase showed 27.4% retained activity.

EXAMPLE 5

Portions of soybean oil were poured into 5 different petri dishes and the enzyme-monomer solution prepared as described in Example 1 was injected drop by drop into the oil at room temperature (about 20° C.).

Gamma irradiation was conducted (60.1 Krad) at room temperature in an unfrozen stage, filtered, washed with a detergent and water. A bead-shaped immobilized enzyme (2-9 mm diameter) along with semicircular beads was obtained. 1/50th of the total preparation was washed, weighed and reacted as in Example 1. The retained activity of the immobilized enzyme was 19.7%.

EXAMPLE 6

An enzyme-monomer solution was prepared by mixing 2 ml of 30% aqueous acrylamide, 2 ml of 30% aqueous calcium acrylate, 0.1 ml divinyl sulfone and 1 ml neutral protease (20 mg/ml). To toluene cooled in a dry ice-acetone mixture, the enzyme, the enzyme-monomer solution was injected.

The solution was frozen as small beads and radio copolymerized with a dose of 550 Krad by $Co^{60}$ gamma rays. After filtration, reliquefaction (thawing) at room temperature and washing, bed-shaped immobilized invertase (1–5 mm diameter) was obtained. 1/50th of the total preparation was mixed with 1 ml of 1% milk casein, 3 ml of phosphate buffer (pH 8.0) and 5 ml of distilled water and reacted at 37° C. for 25 minutes. The reaction was stopped by adding 4 ml of 0.4M trichloro acetate to the reaction mixture, and incubating the resulting mixture at 37° C. for 20 minutes. The solution so obtained was filtered and 5 ml of 0.4M $Na_2CO_3$ and 1 ml of Folin reagent were added to 1 ml of filtrate. The resulting mixture was incubated at 37° C. for 25 minutes. Finally, the optical density of the incubated mixture was measured at 660 mμ.

For comparision purposes, native neutral protease (0.2 mg/ml) was reacted similarly. Bead-shaped immobilized netural protease showed 6.5% of retained activity.

EXAMPLE 7

1 ml of enzyme-monomer solution prepared as described in Example 1 was mixed with 10 ml of soybean oil and shaked vigorously. After freezing in a dry ice-acetone mixture, it was radio copolymerized with $Co^{60}$ gamma ray (83.2 Krad of dose), thawed at room temperature and filtered.

Small bead-shaped immobilized invertase (0.1–1 mm diameter) was obtained. 1/10th of it was submitted for activity assay as Example 1. The retained activity was 67.7%.

EXAMPLE 8

An enzyme monomer solution was prepared as in Example 1 and 0.2 ml of it was added to 10 ml of n-hexane containing 1 to 2 drops of a surface active reagent (such as polyoxyethylene sorbitan monolaurate; Tween 20) and shaked vigorously. Then, the enzyme-monomer solution was dispersed throughout n-hexane and a very small bead-shaped solution was formed. It was then frozen in the coolant and radio copolymerized with a dose of 184.5 Krad of $Co^{60}$ gamma rays. After being melted at room temperature, small bead-shaped immobilized invertase (0.01–0.05 mm of diameter) was obtained. After washing thoroughly with water, 1/10th of it was submitted for activity assay as Example 1 and this shows 71.4% retained activity.

EXAMPLE 9

An enzyme-monomer solution was prepared by mixing 1 ml of 20% aqueous 1-vinyl-2-pyrrolidone, 1 ml of 30% aqueous sodium acrylate, 2 ml of 30% aqueous calcium acrylate, 1 ml of 1.6% N,N'-methylene bis-acrylamide and 100 mg of glucose isomerase producing microorganisms. The thus produced enzyme-monomer solution was treated as in Example 1, except that soybean oil was substituted with toluene and the irradiation dose was increased to 184.5 Krad from 83.2 Krad. Thus, bead-shaped immobilized glucose isomerase was obtained.

To measure the activity of this immobilized enzyme, 1/20th of it was washed with a detergent and water; 2 ml of 30% glucose solution, 1 ml of $MgSO_4$ (1/10 M) and 5 ml of phosphate buffer (1/10 M, pH 7.5), were added and the resulting mixture was reacted at 60° C. for 20 minutes. To 1 ml of the reacted solution was added 4 ml of ½ $M-HClO_4$ to stop the reaction. Then, the resulting reaction mixture was diluted with water, and the resulting fructose was assayed by the Cysteine-Carbasol method.

For comparison purposes, native glucose isomerase producing microorganisms (5 mg) was reacted similarly. The immobilized enzyme showed a retained activity of 15.4%.

EXAMPLE 10

An enzyme monomer solution was prepared by mixing 3 ml of 20% aqueous 1-vinyl-2-pyrrolidone, 1 ml of 30% aqueous calcium acrylate, 0.1 ml of divinyl sulfone and 1 ml of invertase (2 mg/ml). The thus obtained enzyme-monomer solution was treated as Example 1, except that petroleum ether was used instead of soybean oil and the irradiation dose was increased to 184.5 Krad from 83.2 Krad. A bead-shaped immobilized invertase (3 mm diameter) was obtained. 1/20th of it was submitted for activity assay as in Example 1. The retained activity is 25.1%.

EXAMPLE 11

Lipase (1.0 g) was absorbed in SE sephadex (0.1 g) dispersed in 20 ml of water. This absorbed lipase referred to as L hereafter was mixed with other monomers as shown in Table I.

Table I

| | L | A ca | A A | A Na | HEMA | P | DS |
|---|---|---|---|---|---|---|---|
| No. 1 | 1 ml | 2 ml | 2 ml | — | — | — | — |
| No. 2 | 1 " | 2 " | 1 " | 1 ml | — | — | — |
| No. 3 | 1 " | 1 " | 1 " | — | — | 2 ml | — |
| No. 4 | 1 " | 1 " | — | 1 ml | 2 ml | — | 0.1 ml |

L: Lipase absorbed in SE sephadex
A ca: 30 % aqueous solution of calcium acrylate
A A: acrylamide 30 g and N, N'-bis-acrylamide 1.6 g in 100 ml distilled water
A Na: 30 % aqueous solution of sodium acrylate
HEMA: 30 % aqueous solution of hydroxy ethyl methacrylate
P: 20 % aqueous solution of 1-vinyl-2-pyrrolidone
DS: divinyl sulfone Mixed solutions Nos. 1–4 were injected separately into portions of cooled n-hexane, frozen, and radio copolymerized with 850 Krad of $Co^{60}$ gamma rays. After irradiation, n-hexane was discarded. The frozen polymer was melted by using cool water at room temperature. Bead-shaped immobilized lipase was obtained.

A part of the immobilized lipase (0.1–1.0 g) from each mixed solution, Nos. 1–4, was mixed with 2.4 ml of olive oil, 1 ml of $CaCl_2$ (M/10) and 9 ml of acetate buffer (M/10, pH 5.8) and reacted at 30° C. for 30 minutes while stirring at 600 r.p.m. The reaction was stopped by adding 40 ml of ethanol and titrated with N/20 NaOH until the solution has a pH of 9.0.

For comparison purposes, native lipase solution was reacted similarly and the immobilized bead-shaped lipases Nos. 1–4 showed 36.6, 34.8, 42.5 and 13.5% of retained activities, respectively.

In sample No. 1, 0.5 ml of L and 0.5 ml of carbon gelatin colloid (Japanese Sumi), 2 ml of A ca and 2 ml of A A were mixed. When treated as described above, bead-shaped immobilized lipase was obtained which is of black to gray color depending on the intensity of blackness of carbon gelatin colloid. The bead-shaped immobilized lipase had nearly the same retained activity as uncolored beads.

EXAMPLE 12

An enzyme monomer solution was prepared by mixing 4 ml of 30% aqueous magnesium acrylate, 80 mg of N,N'-methylene bis-acrylamide and 1 ml of crude glucose isomerase (45.5 mg/ml). The thus obtained enzyme monomer solution was injected into cooled xylene which was further cooled in a dry ice-acetone mixture.

Gamma irradiation of 550 Krad by $Co^{60}$ was conducted and at room temperature the mixture was melted, filtered, washed with water.

For the purpose of measuring the activity of the immobilized enzyme, 1/50th of it was used. To this, 1 ml of water and 5 ml of substrate were added and reacted at 60° C for 60 minutes.

The reaction was terminated by adding 2 ml of 0.2 M perchloric acid. The resulting fructose content was measured by the Cysteine-Carbazole method.

For comparison purposes, native crude glucose isomerase (0.91 mg) was reacted similarly. As a result, bead-shaped immobilized glucose isomerase showed a retained activity of 78.4%.

Immobilized glucose isomerase was recovered after enzyme reaction and used repeatedly. Even after 10 times use, it showed 68.8% retained activity.

In this experiment the substrate which is composed of 0.2 M glucose, 0.01 M magnesium sulfate and 0.02 M phosphate buffer (pH 7.2) was used. When the substrate has no magnesium ions, native glucose isomerase showed no enzymic activity while immobilized glucose isomerase thus prepared still showed 78.3% retained activity without magnesium ions.

EXAMPLE 13

The same procedure was followed as in Example 12. The difference was substitution of 12% magnesium acrylate (2 ml) and 12% cobalt acrylate (2 ml) for 30% magnesium acrylate (4 ml).

As a result, bead-shaped immobilized glucose isomerase showed 66.5% retained activity.

EXAMPLE 14

An enzyme monomer solution was prepared by mixing 4 ml of 30% aqueous magnesium methacrylate, 80 mg of N,N'-methylene bis-acrylamide and 1 ml of crude glucose isomerase (45.5 mg/ml). The thus obtained enzyme monomer solution was injected into ethyl ether which was cooled in a liquid nitrogen solution. The frozen enzyme-monomer solution was radio copolymerized with $Co^{60}$ gamma ray (274 Krad), thawed at room temperature and filtered.

Small bead-shaped immobilized glucose isomerase ws obtained. 1/50th of it was submitted for activity assay as Example 12. The retained activity of this preparation was 73.4%.

EXAMPLE 15

An enzyme monomer solution was prepared by mixing 2 ml of 15% magnesium acrylate, 2 ml of 12% ferrous acrylate, 80 mg of N,N'-methylene bis-acrylamide and 1 ml of crude glucose isomerase (45.5 mg/ml). The thus obtained enzyme monomer solution was injected into cooled amyl alcohol and the frozen bead was gamma irradiated with 274 Krad by $Co^{60}$.

After thawing at room temperature, 1/50th of it was washed with water and submitted for assaying enzymatic activity as Example 12. As a result, the retained activity was 68%.

EXAMPLE 16

An enzyme monomer solution was prepared by mixing 1 ml of 30% potassium acrylate, 2 ml of 30% acrylamide, 1 ml of 12% nickel acrylate, 60 mg of N,N'-methylene bis-acrylamide and 1 ml of invertase (2 mg/ml).

The thus obtained enzyme monomer solution was injected into methyl ethyl ketone which was cooled in a dry ice-acetone solution. The frozen bead was radio copolymerized with $Co^{60}$ gamma ray (274 Krad).

The activity of immobilized invertase was measured as Example 1 and the retained activity was 72.7%.

EXAMPLE 17

In Example 12, 4 ml of 30% Magnesium acrylate was mixed with 1 ml of crude glucose isomerase, and thus N,N'-methylene bis-acrylamide was not added. Other procedures were similarly conducted. As a result, the obtained bead-shaped immobilized glucose isomerase showed 24.4% retained activity.

What is claimed is:

1. Process for producing an immobilized enzyme in bead form, which comprises adding (i) an aqueous solution containing (a) an enzyme and (b) at least one polymerizable substance capable of being radiopolymerized, said substance being selected from the group consisting of acrylamide, acrylic acid, methacrylic acid, sodium acrylate, potassium acrylate, calcium acrylate, magnesium acrylate, ferrous acrylate, cobalt acrylate, nickel acrylate, magnesium methacrylate, ferrous methacrylate, cobalt methacrylate, nickel methacrylate, acrylonitrile, propylene glycol, pyrrolidone, 1-vinyl-2-pyrrolidone, hydroxy ethyl methacrylate, hydroxy methyl acrylamide, diacetone acrylamide, and polyvinyl alcohol having a polymerization degree of 1400, to (ii) a water-insoluble fluid or a fluid having a solubility in water of up to about 15 percent, whereby beads containing said enzyme are formed in the resulting mixture, freezing the resulting mixture at a temperature of from −200° C. to −5° C., irradiating the resultant frozen mixture at said temperature under aerobic conditions with a dose of radiation of from 30 to 1000 Krad of ionizing radiation to polymerize said polymerizable substance, and recovering polymer beads containing an enzyme immobilized therein.

2. The process of claim 1, wherein water-soluble diethylamino ethyl methacrylate or water-soluble divinyl sulfone is included in (i).

3. The process of claim 1, wherein a cross-linking agent selected from the group consisting of N,N-methylene bis-acrylamide and divinyl sulfone is included in (i).

4. The process of claim 1, wherein the fluid (ii) is selected from the group consisting of soybean oil, sesame oil, olive oil, a light hydrocarbon oil, n-hexane, petroleum ether, a gasoline, toluene, a xylene, a butyl alcohol, an amyl alcohol, ethyl ether, ethyl acetate and methyl ethyl ketone.

5. The process of claim 1, wherein said fluid (ii) contains a surface active agent.

6. The process of claim 1, wherein said ionizing radiation is effected with $Co^{60}$, $Cs^{137}$ or X-rays.

* * * * *